United States Patent [19]

Prescher et al.

[11] Patent Number: 4,762,953

[45] Date of Patent: Aug. 9, 1988

[54] METHOD FOR THE PREPARATION OF SUBSTITUTED TRIHYDROXYBENZENES

[75] Inventors: Guenter Prescher, Hanau; Gebhard Ritter, Darmstadt; Holger Sauerstein, Grosskrotzenburg, all of Fed. Rep. of Germany

[73] Assignee: Degussa Aktiengesellschaft, Frankfurt, Fed. Rep. of Germany

[21] Appl. No.: 19,093

[22] Filed: Feb. 26, 1987

[30] Foreign Application Priority Data

Mar. 11, 1986 [DE] Fed. Rep. of Germany ....... 3607923

[51] Int. Cl.$^4$ .............................................. C07C 37/60
[52] U.S. Cl. .................................... 568/771; 568/763
[58] Field of Search ............................. 568/771, 763

[56] References Cited

U.S. PATENT DOCUMENTS 4,351,968  9/1982  Harris .................................. 568/771
4,469,899  9/1984  Nakamura .......................... 568/763

FOREIGN PATENT DOCUMENTS 0046918   3/1982   European Pat. Off. ........... 568/763
1228258  11/1966   Fed. Rep. of Germany .
2064497   7/1971   Fed. Rep. of Germany .
2410758   7/1975   Fed. Rep. of Germany .
151832  12/1975   Japan ................................. 568/771

*Primary Examiner*—Werren B. Lone
*Attorney, Agent, or Firm*—Beveridge, DeGrandi & Welacher

[57] ABSTRACT

A method for the production of substituted 1,2,3- and 1,2,4-trihydroxybenzenes in a single process reaction step, wherein the corresponding substituted resorcinol which is a substituted 1,3-dihydroxybenzene is contacted with an aqueous hydrogen peroxide solution and through control of the water content of the initial reaction condition and control of the reaction temperature the desired products are obtained.

11 Claims, No Drawings

METHOD FOR THE PREPARATION OF SUBSTITUTED TRIHYDROXYBENZENES

The present invention relates to a method for the preparation of mixtures of substituted 1,2,3- and 1,2,4-trihydroxybenzenes.

The above-identified compounds are important intermediates for various syntheses of products in the pharmaceutical, cosmetic, agricultural and photochemical industries. See for example Kirk-Othmer, Encyclopedia of Chemical Technology, 3rd Edition, Vol. 18, p. 670–84, 1982.

Up until the present invention, these compounds could only be prepared utilizing very expensive multiple step processes.

According to the description in European patent No. 25 659, substituted pyrogallol compounds can be prepared, for example, through chlorination of 2,6-dimethylphenol derivatives to produce the corresponding chloro-compounds, wherein the chloromethyl groups are then converted into aldehyde groups. The aldehydes are then oxidized according to the Dakin reaction with percompounds, such as hydrogen peroxide or peracids or their corresponding salts, in basic or alkaline medium to the desired pyrogallol compounds. These multi-step processes lead only to meager yields in spite of the considerable effort.

A further multi-step method which involves a modification of the Dakin reaction and which involves the formation of hydroxybenzaldehyde leads only then to satisfactory yields when the pH value is held constant at 6 during the reaction by the addition of bases. As a result, the purification thereof is made more difficult. See European patent No. 44,260.

Another inconvenient method with more variable yields of pyrogallol or pyrogallol-compounds is described in DE-OS No. 26 53 446. In accordance therewith, a compound is first prepared which is 2,2,6,6-tetrahalogencyclohexanone, which is then hydrolyzed with water in the presence of a catalyst or hydrolyzed in the form of an alkoxide with an acid.

Other attempts which have involved conversion of diaminophenols to polyhydroxy compounds have not led to good results and were also considerably costly. See DE-OS No. 24 43 336.

A further possible process which involves the Thiele-Winter reaction leading to hydroxyhydroquinones or substituted polyhydroxy compounds is known, but has been found to be very cumbersome and costly. The reaction resides in the conversion of a corresponding quinone into hydroxyhydroquinone through the acetoxylation thereof with acetic anhydride in the presence of sulfuric acid or borofluoroetherate to the corresponding triacetate and then the conversion thereof into the desired hydroxyhydroquinone or the substituted polyhydroxy compound. See DE-OS No. 24 59 059.

It is accordingly the object of the present invention to provide a method for the direct synthesis of the corresponding 1,2,3- and 1,2,4-trihydroxybenzenes starting from the substituted resorcinols.

It has now been found that mixtures of substituted 1,2,3- and 1,2,4-trihydroxybenzenes can be prepared in a one-step method by utilizing substituted resorcinols of the formula:

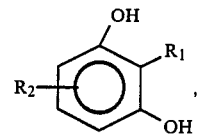

wherein $R_1$ and $R_2$ represent hydrogen, aliphatic saturated straight chain or branched chain hydrocarbon residues containing from 1 to 6 carbon atoms, or —COOH, —COOR$_3$, —CH$_2$OR$_3$, —SO$_3$H, —NO$_2$, NH$_2$, or F, Cl, Br, and I; $R_3$ represents an aliphatic, saturated straight chain or branched chain hydrocarbon residue containing 1 to 6 carbon atoms, and $R_1$ and $R_2$, with the exception of hydrogen, can be the same or different, wherein an aqueous hydrogen peroxide is reacted with the said substituted resorcinol at a temperature of 60° to 150° C. and wherein the initial amount of water present in the mixture at the beginning of the reaction ranges from 0.1 to 36% by weight, based on the total weight of the mixture.

The resorcinols which can be used for purposes of the present invention are illustratively 2-methylresorcinol; 5-methylresorcinol (Orcin); 4n-hexylresorcinol; 2,5-dimethylresorcinal (β-orcin); 4-chlororesorcinol; 4,6-dichlororesorcinol, dihydroxybenzoic acid. Preferably, there is to be mentioned 2-methylresorcinol and dihydroxybenzoic acid. Resorcinol itself is not used in accordance with the present invention.

The resorcinol compounds that are introduced and that may be used in general in accordance with the present invention are of commercial purity. Preferably, they are introduced as molten melts so long as the melting point is sufficiently low that they can be mixed with hydrogen peroxide without causing any potentially dangerous mixtures.

In the event that the resorcinols selected for utilization in accordance with the present invention have melting points which are near to or above the boiling point of the hydrogen peroxide which is used, then in that case they should be utilized in the form of a solution in water or in an organic solvent.

The selection of the organic solvent should be carried out so that its boiling point is in the range of the desired operational temperature at which the process is to be carried out.

It is also suitable and desirable when using aqueous solutions of the resorcinol compound or solutions in organic solvent materials preferably to use the saturated solutions so that the reaction velocity is not unnecessarily reduced.

As the suitable solvent material that can be used in accordance with the present invention there can be mentioned the conventional solvents, such as for example aliphatic carboxylic acid esters, e.g., ethyl-, propyl-, n-butyl-, secbutyl-, tert. butyl-, n-hexylesters of acetic acid, and in addition to that chlorinated hydrocarbons, such as chloroform, carbon tetrachloride, methylchloride or aromatic hydrocarbons, such as benzene or toluol can be used.

The aqueous hydrogen peroxide solutions that can be used for purposes of the present invention are the conventional and commercially available solutions having concentrations in the range of 20 to 85 weight percent hydrogen peroxide, preferably 50 to 85 weight percent.

Suitable initial starting temperatures which are used for bringing the resorcinol into contact with the hydrogen peroxide are in the range of 90° to 120° C.

Preferably, the amount of water present at the initiation of the reaction ranges from about 0.5 to 15 weight percent, preferably about 0.5 to 10 weight percent, based on the mixture which exists before the initiation of the reaction. Most preferably, the amount of water is in the range of 0.5 to 6 weight percent.

The molar ratio of resorcinol compound to hydrogen peroxide lies in the range of 2 to 20:1, preferably 5 to 10:1.

The technical advantage of the method of the present invention includes, inter alia, the ability to utilize commercially available starting materials and to provide in a single-stage reaction method a synthetic route that leads to the desired 1,2,3- and 1,2,4-trihydroxybenzenes. In this way, additional preparative methods for obtaining very special starting materials are not needed.

It has also been determined that the length of the essential conversion reaction is considerably shortened and in spite of this, favorable yields are obtained.

The prior art, such as Wurster, in Berichte, Vol. 10, p. 2939, 1887, described a method in contrast to the present invention, wherein orcin was treated with aqueous hydrogen peroxide and lead only to the formation of a dye or coloring material.

The present invention is illustrated in the following examples.

EXAMPLE 1

38.53 g (0.25 mole), 2,6-dihydroxybenzoic acid is dissolved in 30 g n-propylacetate and is then heated to boiling at 110° C. To this stirred solution there is then added 2.76 g (0.055 mole) 70% hydrogen peroxide. The temperature in the reaction solution then rises thereafter to about 120° C. After subsidence of the exothermic reaction there is determined after 10 minutes that the hydrogen peroxide conversion is 100%. The reaction mixture contains then 6.9 g (0.040 mole) 2,3,6-trihydroxybenzoic acid, which corresponds to a total yield of 74.7%, based on the hydrogen peroxide that is introduced into the reaction.

EXAMPLE 2

12.4 g (0.1 mole) 2-methylresorcinol is heated up to 120° C. To the stirred melt there is then introduced 1.25 g (0.025 mole) of a 70% hydrogen peroxide solution. The temperature in the reaction solution increases by exothermic reaction to 150° C. After subsidence of the exotherm there is determined after 10 minutes to be a conversion of the hydrogen peroxide of 100%. The reaction mixture contains then 2.56 g (0.018 mole) 2,3,6-trihydroxytoluol, which corresponds to a total yield of 73.2%, based on the hydrogen peroxide that is introduced into the reaction system.

Further variations or modifications of the present invention will be apparent to those skilled in the art from the foregoing and are intended to be encompassed by the claims appended hereto.

The German priority application No. P 36 07 923.5 is relied on and incorporated by reference.

We claim:

1. A method for the preparation of substituted 1,2,3- and 1,2,4-trihydroxybenzenes comprising contacting a compound which is a substituted resorcinol represented by the structural formula:

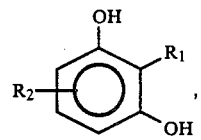

wherein $R_1$ and $R_2$ represent hydrogen, aliphatic, saturated, straight or branched chain hydrocarbons containing 1 to 6 carbon atoms, or —COOH, —COOR$_3$, —CH$_2$OR$_3$, —SO$_3$H, —NO$_2$, NH$_2$, F, Cl, Br, or I;

$R_3$ represents an aliphatic saturated straight or branched chain hydrocarbon with 1 to 6 carbon atoms;

and R and $R_1$, with the exception of hydrogen, can be the same or different, with aqueous hydrogen peroxide at a temperature of 60° to 150° C., wherein the amount of water present in the reaction composition at the initiation of the reaction is between 0.1 and 36 weight percent, and continuing the reaction to obtain the desired trihydroxybenzenes.

2. The method in accordance with claim 1, wherein the substituted resorcinol is: 2-methylresorcinol, 5-methylresorcinol, 4n-hexylresorcinol, 2,5-dimethylresorcinol, 4-chlororesorcinol, 4,6-dichlororesorcinol or dihydroxybenzoic acid.

3. Method in accordance with claim 1, wherein the resorcinol is 2-methylresorcinol or dihydroxybenzoic acid.

4. The method in accordance with claim 1, wherein dimethylresorcinol is used in the form of molten melt.

5. The method in accordance with claim 1, wherein the reactions are carried out at a temperature of 90° to 120° C.

6. The method in accordance with claim 1, wherein the amount of water present in the reaction system at the beginning of the reaction is between 0.5 and 15 weight percent, based on the total weight of the mixture of resorcinol and hydrogen peroxide.

7. The method in accordance with claim 1, wherein the amount of water present in the reaction system at the initiation of the reaction is between 0.5 and 10 weight percent, based on the reaction mixture containing the substituted resorcinol and hydrogen peroxide.

8. Method in accordance with claim 1, wherein the amount of water present in the reaction system at the intiation of the reaction is between 0.5 and 6 weight percent, based on the total weight of the composition containing the substituted resorcinol or the hydrogen peroxide.

9. The method in accordance with claim 1, wherein the ratio of resorcinol to hydrogen peroxide is 5–10:1.

10. The method in accordance with claim 1, wherein the reaction is carried out in the absence of catalysts.

11. The method in accordance with claim 1, wherein the reaction is carried out in the presence of stirring.

* * * * *